United States Patent
Iwase et al.

(10) Patent No.: US 12,286,573 B2
(45) Date of Patent: Apr. 29, 2025

(54) ADHESIVE SHEET

(71) Applicants: MEKTEC CORPORATION, Tokyo (JP); OSAKA UNIVERSITY, Osaka (JP)

(72) Inventors: Masayuki Iwase, Osaka (JP); Teppei Araki, Osaka (JP); Tsuyoshi Sekitani, Osaka (JP); Shusuke Yoshimoto, Osaka (JP)

(73) Assignees: Mektec Corporation, Tokyo (JP); Osaka University, Osaka (JP)

( * ) Notice: Subject to any disclaimer, the term of this patent is extended or adjusted under 35 U.S.C. 154(b) by 181 days.

(21) Appl. No.: 16/817,352

(22) Filed: Mar. 12, 2020

(65) Prior Publication Data

US 2020/0291274 A1 Sep. 17, 2020

(30) Foreign Application Priority Data

Mar. 12, 2019 (JP) .................. 2019-045152

(51) Int. Cl.
*C09J 9/02* (2006.01)
*A61B 5/257* (2021.01)
(Continued)

(52) U.S. Cl.
CPC ............. *C09J 9/02* (2013.01); *A61B 5/257* (2021.01); *A61N 1/0452* (2013.01);
(Continued)

(58) Field of Classification Search
None
See application file for complete search history.

(56) References Cited

U.S. PATENT DOCUMENTS

| | | | |
|---|---|---|---|
| 7,208,226 B2 * | 4/2007 | Yamashita | C09J 7/10 428/354 |
| 9,096,779 B2 * | 8/2015 | Kim | H01B 1/00 |
| 9,159,940 B2 * | 10/2015 | Kato | C09J 11/06 |
| 11,145,467 B2 * | 10/2021 | Tsutsumi | H01G 9/0036 |

(Continued)

FOREIGN PATENT DOCUMENTS

| | | | |
|---|---|---|---|
| JP | 2001-238860 A | | 9/2001 |
| JP | 2004047915 A | * | 2/2004 |

(Continued)

OTHER PUBLICATIONS

Machine translation of JP 2004047915 A (Year: 2004).*
Notice of Reasons for Refusal issued in Japanese Application No. 2019-045152, dated Oct. 25, 2022.

*Primary Examiner* — Frank D Ducheneaux
(74) *Attorney, Agent, or Firm* — Knobbe, Martens, Olson & Bear, LLP

(57) ABSTRACT

To provide an adhesive sheet, the sheet increasing manufacturing efficiency of products including an adhesive agent layer, while using the adhesive agent layer to which an electro-conductive organic polymer compound is added. An adhesive sheet for use in applying a wiring board to a surface onto which the wiring board is to be applied, the adhesive sheet is constituted by an adhesive agent layer including an electro-conductive organic polymer compound and an adhesive material; a first releasing sheet provided on front surface of the adhesive agent layer; and a second releasing sheet provided on a back surface corresponding to a back surface of the front surface in the adhesive agent layer.

16 Claims, 7 Drawing Sheets

(51) Int. Cl.
  *A61N 1/00*    (2006.01)
  *A61N 1/04*    (2006.01)
  *C09J 7/40*    (2018.01)
  *H05K 1/00*    (2006.01)
  *H05K 1/09*    (2006.01)
  *H05K 1/02*    (2006.01)

(52) U.S. Cl.
  CPC .............. *A61N 1/0492* (2013.01); *C09J 7/40* (2018.01); *H05K 1/095* (2013.01); *C09J 2203/326* (2013.01); *C09J 2301/204* (2020.08); *C09J 2301/30* (2020.08); *C09J 2301/314* (2020.08); *C09J 2433/00* (2013.01); *C09J 2481/00* (2013.01); *H05K 1/0283* (2013.01); *H05K 2201/0329* (2013.01); *H05K 2201/10151* (2013.01)

(56) References Cited

U.S. PATENT DOCUMENTS

| 2008/0145572 A1* | 6/2008 | Yano ........................ C09J 7/29 |
| | | 428/1.54 |
| 2008/0191174 A1* | 8/2008 | Ehrensvard .............. H01R 4/04 |
| | | 252/500 |
| 2009/0258225 A1* | 10/2009 | Nishida ................... B32B 27/36 |
| | | 428/352 |

FOREIGN PATENT DOCUMENTS

| JP | 2007-051173 A | 3/2007 |
| JP | 2012-017399 A | 1/2012 |
| JP | 2016-089021 A | 5/2016 |
| JP | 2017-057256 A | 3/2017 |
| JP | 2017-186486 A | 10/2017 |
| WO | WO 2018/101438 A1 | 6/2018 |

* cited by examiner

ADHESIVE SHEET

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is based on and claims the benefit of priority from Japanese Patent Application No. 2019-045152, filed on 12 Mar. 2019, the content of which is incorporated herein by reference.

BACKGROUND OF THE INVENTION

Field of the Invention

The present invention relates to an adhesive sheet applied to a surface to be affixed, by way of adhesiveness.

Related Art

In recent years, there has been a growing trend of healthcare-oriented life style throughout society, reduction in increasing medical expense, and utilization of big data in the IoT (Internet of Things) society. Against these backgrounds, there is increasing social demand to acquire weak signals (biosignals) obtained from living bodies in various environments. The biosignal is acquired, for example, by mounting an element having, for instance, a function of receiving a biosignal on a board on which a wiring or the like is formed, and applying the board to a surface of skin (hereinafter, simply referred to as "skin surface") of a living body. As the board used in this context, an stretchable circuit board capable of stretching and shrinking depending upon the movement of the living body is suitable. The stretchable circuit board is applied to the skin surface of the living body by an adhesive agent layer. In the present specification, a device formed by combining an element, an stretchable circuit board, and an adhesive agent layer is also referred to as a biosensor hereinafter.

The adhesive agent layer used for biosensors is required not to detach from the skin surface due to movement of the living body and to provide the living body with as little pain as possible when peeled from the skin surface. In many cases, stretchable circuit boards are made disposable, but the adhesive agent layer is required to be able to be reapplied considering reapplication to the skin surface. In addition, the adhesive agent layer used for biosensors is required to be electrically conductive to transfer a biosignal between the skin surface and the stretchable circuit board. A conductive filler is provided to the adhesive agent layer, for the adhesive agent layer to be electrically conductive. Examples of the conductive filler include graphite-based, metal-based, metal oxide-based, metal coating-based and metal oxide coating-based type, etc., and it is preferable to use an electro-conductive organic polymer compound which has little effect on the living body as the adhesive material, which is directly applied to the living body.

Adding an electro-conductive organic polymer compound to a tacky adhesive agent to form an antistatic tacky adhesive agent is described in, for example, Patent Document 1. Patent Document 1 discloses that an antistatic tacky adhesive agent is applied to a base material to form a protective film.

Patent Document 1: Japanese Unexamined Patent Application, Publication No. 2007-51173

SUMMARY OF THE INVENTION

However, when a tacky adhesive agent (adhesive agent) is directly applied to a base material and dried, as described in Patent Document 1, time required for the tacky adhesive agent to dry is added to the time required from the beginning to the end of the production of the product, and this lowers throughput of the production of the product. The present invention has been made in view of the above-mentioned problems, and the present invention relates to an adhesive sheet, which comprises an electro-conductive organic polymer compound, and use of which enables production efficiency of products comprising this adhesive agent layer to be increased.

The inventive adhesive sheet is an adhesive sheet for use in applying a wiring board to a surface to which the wiring board should be applied, and the adhesive sheet comprises: an adhesive agent layer comprising an electro-conductive organic polymer compound and an adhesive material; a first releasing sheet provided on a first surface of the adhesive agent layer; and a second releasing sheet provided on a second surface corresponding to a back surface of the first surface in the adhesive agent layer.

The present invention can provide an adhesive sheet, which comprises an electro-conductive organic polymer compound, and use of which enables production efficiency of products comprising this adhesive agent layer to be increased.

DETAILED DESCRIPTION OF THE PREFERRED EMBODIMENT

Figure 1A:
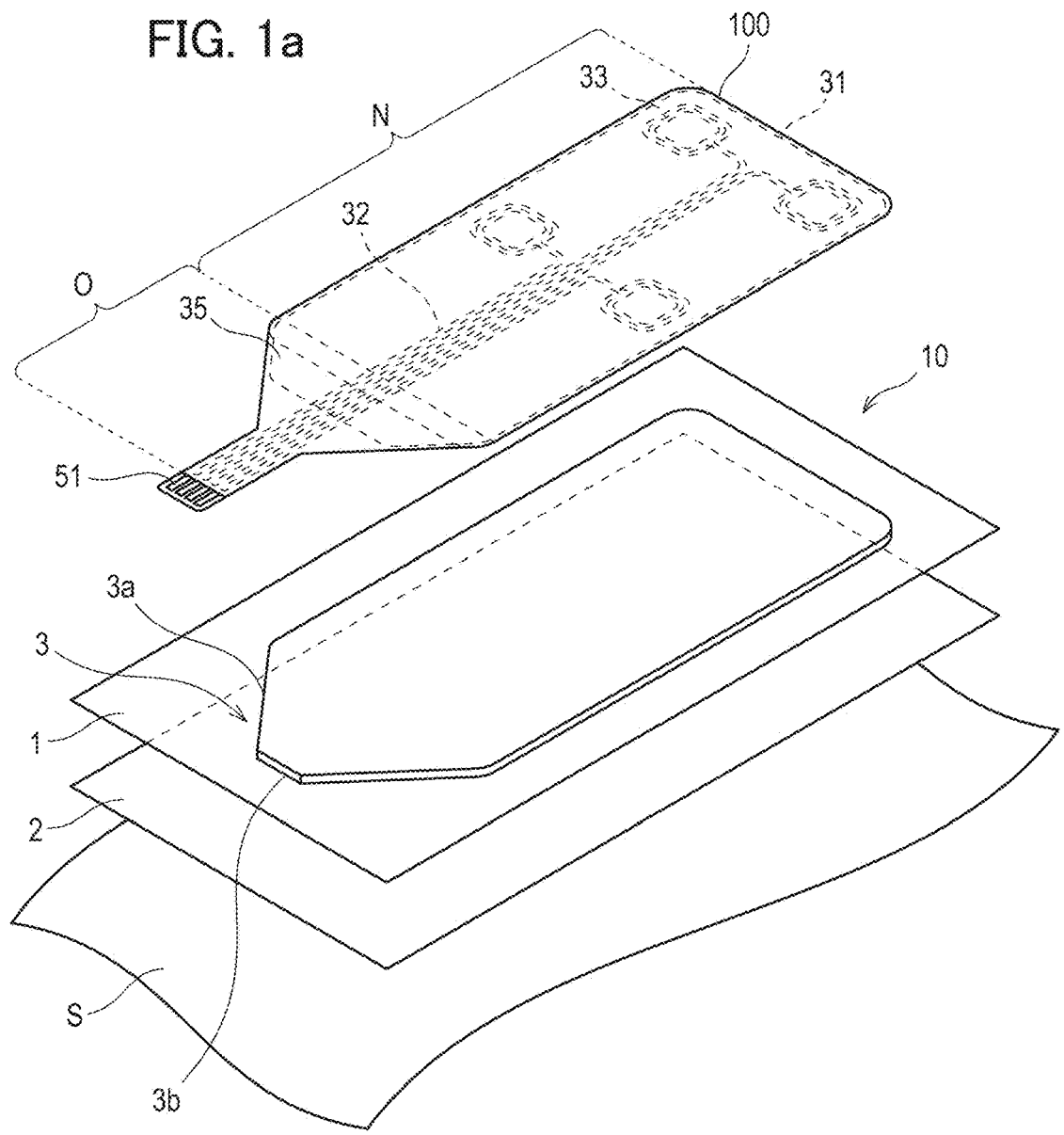
FIG. 1(a) is a schematic perspective view for explaining the adhesive sheet of an embodiment of the present invention.

Hereinafter, an embodiment of the present invention is described with reference to the drawings. In all the drawings, the same components are denoted by the same reference numerals, and redundant descriptions are omitted as appropriate. In addition, the drawings shown in the embodiment and the variation example thereof are schematic diagrams for explaining the configurations and functions, and the like of the adhesive sheet of the present embodiment, and do not necessarily accurately show the dimensions, shapes, lengths, widths, thicknesses and relative proportions thereof.

Figure 1B:
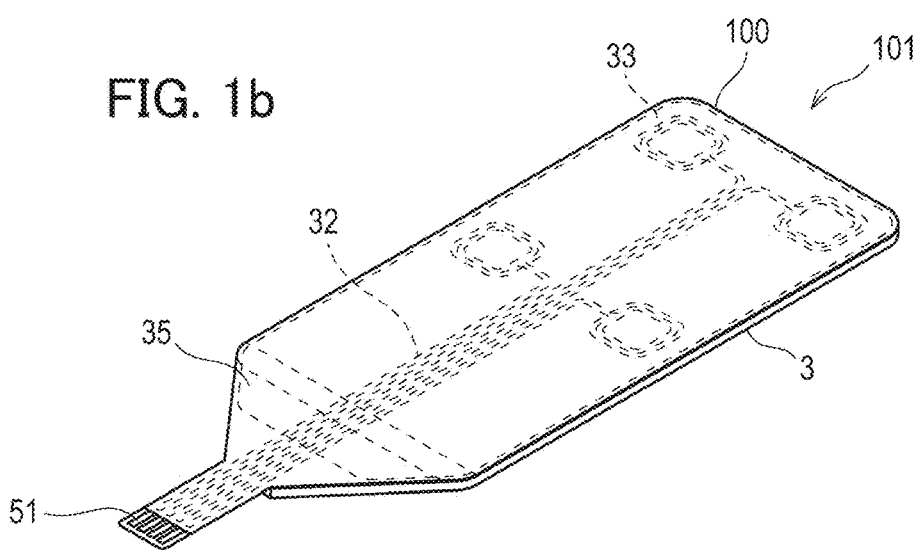
FIG. 1(b) is a schematic perspective view of a biosensor using the adhesive sheet shown in FIG. 1(a)
Figure 2:
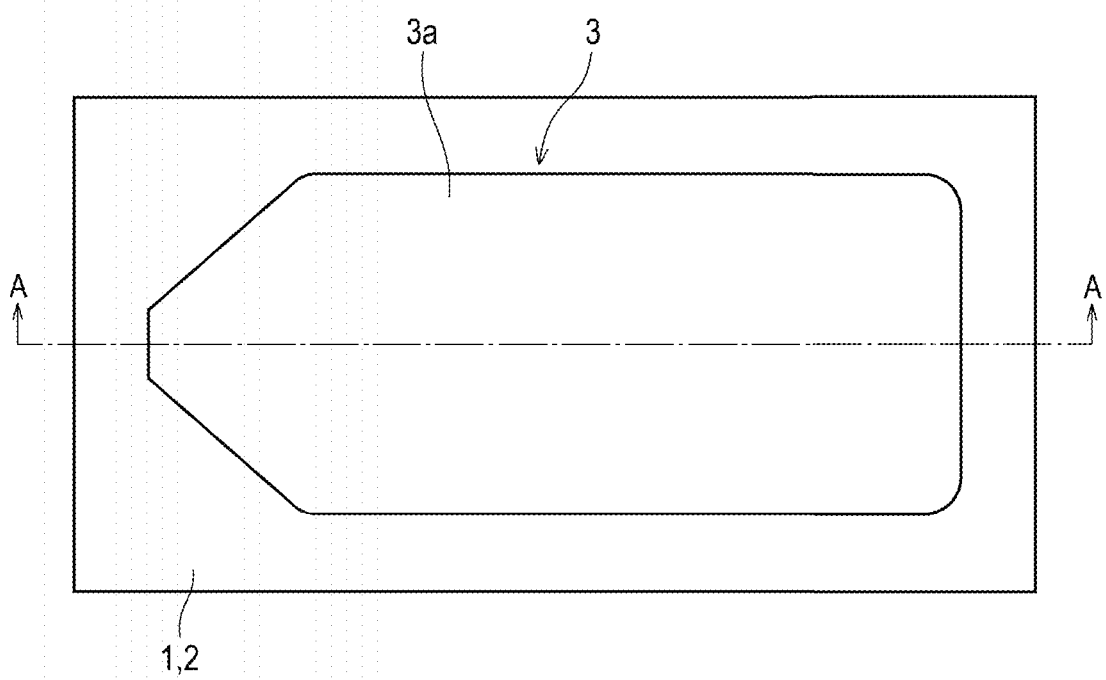
FIG. 2 is a top view of the adhesive sheet shown in FIG. 1.
Figure 3:
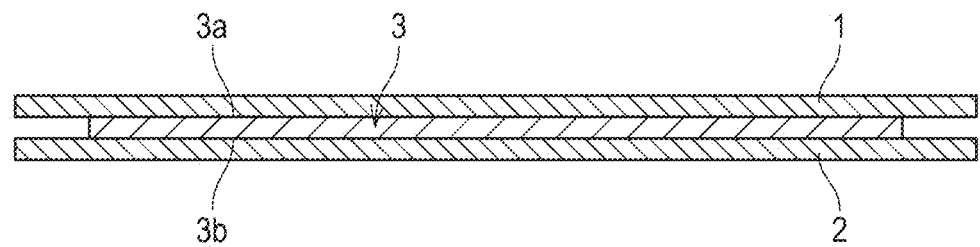
FIG. 3 is a cross-sectional view of the adhesive sheet cut along the dot-and-dash line shown in FIG. 2, and viewed in the direction of arrows A and A.

FIG. 1(a) is a schematic perspective view for explaining adhesive sheet 10 of the present embodiment. FIG. 1(b) is a perspective view of a biosensor 101 formed using an adhesive sheet 10. The illustrated adhesive sheet 10 is an adhesive sheet which is used for applying a wiring board 100 to a surface to which the wiring board 100 should be applied. In FIG. 1(a), the wiring board 100 is shown together with the adhesive sheet 10 for explanation. FIG. 2 is a top view of the adhesive sheet 10 shown in FIG. 1(a), and FIG. 3 is a cross-sectional view of the adhesive sheet 10 cut along the dot-and-dash line shown in FIG. 2, and viewed in the direction of arrows A and A. In the present embodiment, explanation is given by referencing an example in which the wiring board 100 is used as a stretchable board, applied to a body (living body) of a subject, and used in the biosensor 101 for measuring a biosignal such as muscle potential. In the present embodiment, in the state that the adhesive sheet 10 is applied to the skin surface S, the side facing the skin surface S is defined as a back (back surface, back side), and the opposite side of the back is defined as a front (front surface, front side). FIG. 1(a) is a top perspective view of the adhesive sheet 10 as viewed from the back side, and FIG. 2 is a top view of the adhesive sheet 10 as viewed from the front side.

The wiring board 100 has a stretchable base material 31 having stretchability and a film base material 35 having lower stretchability than the stretchable base material 31. Further, the wiring board 100 has stretchable wiring 32. The stretchable wiring 32 is formed over an overlapping region O in which the stretchable base material 31 and the film base material 35 overlap each other and a non-overlapping region N in which both do not overlap each other. In addition to the above-described configuration, the wiring board 100 has an stretchable cover (not shown). The stretchable cover is a member for protecting the stretchable wiring 32 on the stretchable base material 31. An external terminal 51 is formed at one end of the overlapping area O of the wiring board 100, and the stretchable wiring 32 is connected to the external terminal 51. An electrode 33 is connected to the other end of the stretchable wiring 32. The electrode 33 contacts a living body to detect a biosignal. The detected biosignal is inputted from the external terminal 51 to an element mounted on the wiring board 100. A separator (not shown) is provided on the stretchable base material 31 of the wiring board 100 to protect the stretchable base material 31 and prevent the tacky stretchable base material 31 from sticking to an unintentional member or wrinkling.

The adhesive sheet comprises an adhesive agent layer 3, a first releasing sheet 1 provided on a first surface of the adhesive agent layer 3, and a second releasing sheet 2 provided on a second surface corresponding to the back surface of the first surface in the adhesive agent layer 3. Hereinafter, in the present embodiment, the surface facing the wiring board 100 of the adhesive sheet 10 and the adhesive agent layer 3 is defined as a first face, and the surface facing the skin surface S is defined as a second face. Further, the first surface is defined as a "front surface" 3a, and the second surface is defined as a "back surface" 3b. In the adhesive sheet 10 of the present embodiment, the first releasing sheet 1 is first peeled off from the adhesive agent layer 3, and the front surface 3a of the adhesive agent layer 3 is exposed. The exposed front surface 3a contacts the back surface of the wiring board 100 and is pressed into intimate contact. Such a treatment integrates the wiring board 100 and the adhesive agent layer 3. At this time, the wiring board 100 is in close contact with the front surface 3a of the adhesive agent layer 3, and the second releasing sheet 2 is in close contact with the back surface 3b. It should be noted that, as described above, in order to make the first releasing sheet 1 securely and more early peel off than the second releasing sheet 2, it is essential to consider balancing the bonding strength between the adhesive agent layer 3 and the releasing sheets. That is, it is desirable to set the bonding strength between the adhesive agent layer 3 and the first releasing sheet 1 to be lower than the bonding strength between the adhesive agent layer 3 and the second releasing sheet 2. In the above description, the terms "film," "sheet," and "membrane" broadly encompass thin-shaped objects. Namely, the magnitude of the individual thickness is not defined by the difference in the designation of a sheet, a film, a membrane, or the like.

As shown in FIGS. 1 to 3, the first releasing sheet 1 and the second releasing sheet 2 sandwich the adhesive agent layer 3, and their dimensions and shapes are sufficiently larger than those of the adhesive agent layer 3 in the top surface view. The reason for this is to prevent the first releasing sheet 1 and second releasing sheet 2 from peeling off from the adhesive agent layer 3 even if a force is applied to the end portions of the first releasing sheet 1 and the second releasing sheet 2, or to prevent the adhesive agent from being exposed from the end faces, which would be problematic if the first releasing sheet 1 and second releasing sheet 2 were to have the same dimension and shape as the adhesive agent layer 3. As a material for the first releasing sheet 1 and the second releasing sheet 2, resins and papers may be used. As a resin used for first releasing sheet 1 and the second releasing sheet 2, for example, PET (PolyEthylene Terephthalate) film is suitable. The first releasing sheet 1 and second releasing sheet 2 of the present embodiment are formed by using paper or PET film as a base material and coating the base material with a releasing agent. If the board is paper, a barrier layer may be provided between the board and the releasing agent to prevent the releasing agent from seeping into the paper. The releasing agent includes silicone-based type and non-silicone-based type. The silicone-based releasing agent has excellent heat resistance and is therefore suitable for a releasing sheet obtained by a method including a thermocompression step. As the non-silicone-based releasing agent, for example, a fluorine-based releasing agent can be mentioned. A fluorine-based releasing agent is preferred mainly for electronic devices because of its cleanliness (not generating dust), antistatic properties, and highly intimate adhesiveness.

However, the first releasing sheet 1 or the second releasing sheet 2 is not limited to a resin or a paper, and any materials may be used as long as they have such a function and can be easily peeled from the adhesive agent layer 3. In particular, the second releasing sheet 2 to be integrated with the wiring board 100 is required to have flexibility capable of following the wiring board 100. Examples of the resin satisfying such requirements include a film made of a resin such as polyethylene terephthalate, polyethylene naphthalate, tetraacetyl cellulose, syndiotactic polystyrene, polyphenylene sulfide, polycarbonates, polyallylate, polysulfones, polyester sulfones, polyetherimides and cyclic polyolefins, etc. Among others, a resin from which a film having excellent mechanical strength, durability, transparency, and the like can be manufactured is preferable. A thickness of the first releasing sheet 1 or the second releasing sheet 2 is generally from 3 µm to 5 mm, preferably from 5 µm to 1 mm, more preferably from 10 µm to 100 µm, in terms of mechanical strength, durability and transparency.

The adhesive agent layer 3 has a shape and size corresponding to a part of the non-overlapping region N and the entire surface of the overlapping region O in the back surface of the wiring board 100. The reason for this is that when the outer periphery of the adhesive agent layer 3 is smaller than the outer periphery of the wiring board 100, the wiring board 100 is apt to peel off from the outer periphery, and when the outer periphery of the adhesive agent layer 3 is larger than the outer periphery of the wiring board 100, a part of the adhesive agent layer 3 is exposed and sticks to an unintended portion. In the present embodiment, the adhesive agent layer 3 is not provided over a predetermined length from the external terminal 51 in the overlapping area O in the wiring board 100. This is because the portion over a predetermined length from the external terminal 51 is bent and connected to an input terminal of an element (not shown).

The adhesive agent layer 3 includes an electro-conductive organic polymer compound and an adhesive material. At least one of polyanilines, polypyrroles, polythiophenes and derivatives thereof is used as the electro-conductive organic polymer compound. Polyanilines, polypyrroles and polythiophenes are electro-conductive organic polymer compounds having conductivity by n-electron conjugation. The polyanilines are high molecular weight compounds of aniline which is substituted with an alkyl or alkoxy group having 1 to 18 carbon atoms, an aryl group or a sulfonic acid group, etc. at 2- or 3-position or N-position of the aniline. Examples thereof include poly(2-methylaniline), poly(3-methylaniline), poly(2-ethylaniline), poly(3-ethylaniline), poly(2-methoxyaniline), poly(3-methoxyaniline), poly(2-ethoxyaniline), poly(3-ethoxyaniline), poly(N-methylaniline), poly(N-propylaniline), poly(N-phenyl-1-naphthylaniline), poly(8-anilino-1-naphthalenesulfonic acid), poly(2-aminobenzene sulfonic acid) and poly(7-anilino-4-hydroxy-2-naphthalene sulfonic acid), etc.

Examples of derivatives of the polyanilines include polyanilines which are doped or mixed with a dopant. Examples of the dopant include halide ions such as chloride ions, bromide ions and iodide ions, etc.; perchlorate ions; tetrafluoroborate ions; hexafluoro arsenate ions; sulfate ions; nitrate ions; thiocyanate ions; hexafluoro silicate ions; phosphate-based ions such as phosphate ions, phenyl phosphate ions and hexafluoro phosphate ions; trifluoro acetate ions; alkylbenzene sulfonate ions such as tosylate ions, ethylbenzene sulfonate ions and dodecylbenzene sulfonate ions, etc.; alkylsulfonate ions such as methylsulfonate ions and ethylsulfonate ions, etc.; or polymer ions such as polyacrylate ions, polyvinyl sulfonate ions, polystyrene sulfonate ions (PSS) and poly(2-acrylamide-2-methylpropanesulfonic acid) ions, etc. These may be used singly or in combination of two or more.

The polypyrroles are high molecular weight compounds of pyrrole which is substituted with an alkyl or alkoxy group having 1 to 18 carbon atoms at 1- or 3-position or 4-position of the pyrrole. Examples thereof include poly(1-methylpyrrole), poly(3-methylpyrrole), poly(1-ethylpyrrole), poly(3-ethylpyrrole), poly(1-methoxypyrrole), poly(3-methoxypyrrole), poly(1-ethoxypyrrole) and poly(3-ethoxypyrrole), etc. Examples of derivatives of the polypyrroles include polypyrroles which are doped or mixed with a dopant. As the dopant, those described above can be used.

The polythiophenes are high molecular weight compounds of thiophene which is substituted with an alkyl or alkoxy group, etc. having 1 to 18 carbon atoms at 3- or 4-position of the thiophene. Examples thereof include poly (3-methylthiophone), poly(3-ethylthiophone), poly(3-methoxylthiophone), poly(3-ethoxythiophone) and poly(3,4-ethylenedioxythiophone) (PEDOT), etc. Examples of derivatives of the polythiophenes include polythiophenes which are doped or mixed with a dopant. As the dopant, those described above can be used.

In the present embodiment, as the derivative of the polythiophenes, a mixture of polystyrene sulfonate ions (PSS) and poly(3,4-ethyleneoxide thiophene) (PEDOT) as the dopant (hereinafter sometimes referred to as "PEDOT: PSS") is preferable from a viewpoint of high conductivity being able to be obtained, having a hydrophilic skeleton useful for retaining water molecules, and being able to be easily dispersed in water.

The adhesive material forming the adhesive agent layer 3 is an electrically conductive adhesive agent composition comprising an aqueous emulsion adhesive agent. As the aqueous emulsion adhesive agent, there is no particular limitation as long as it has film forming properties and adhesiveness, and acrylic emulsion adhesive agents, vinyl acetate-based emulsion adhesive agents and ethylene-vinyl acetate copolymer-based emulsion adhesive agents or the like can be mentioned. Among the above aqueous emulsion adhesive agents, the acrylic emulsion adhesive agents are preferable in the present embodiment, from a viewpoint of weather resistance, heat resistance, oil resistance, and the like being able to be imparted in addition to adhesiveness and transparency.

Further, providing transparency to adhesive agents generates advantages that various inspections, such as checking foreign matter adhesion or shift in the position of application, come to be easier, when the adhesive agent layer 3 is applied to the wiring board 100. The acrylic emulsion adhesive agents comprise an acrylic copolymer as a main component, and can be produced by emulsion polymerization of unsaturated monomers such as alkyl(meth)alkyl acrylates and functional group-containing monomers and other monomers, if desired, using water as a dispersing medium and usually various types of emulsifier.

As the alkyl (meth)alkyl acrylates, alkyl (meth)acrylates in which the alkyl group has 1 to 20 carbon atoms are preferable. Specifically, examples thereof include methyl (meth)acrylate, ethyl (meth)acrylate, propyl (meth)acrylate, butyl (meth)acrylate, pentyl (meth)acrylate, hexyl (meth) acrylate, cyclohexyl (meth)acrylate, 2-ethylhexyl (meth) acrylate, isooctyl (meth)acrylate, decyl (meth)acrylate, dodecyl (meth)acrylate, myristyl (meth)acrylate, palmityl (meth)acrylate and stearyl (meth)acrylate, etc. These may be used singly or in combination of two or more.

Examples of the functional group-containing monomers include 2-hydroxyethyl (meth)acrylate, 2-hydroxypropyl (meth)acrylate, 3-hydroxypropyl (meth)acrylate, 2-hydroxybutyl (meth)acrylate, 3-hydroxybutyl (meth)acrylate and 4-hydroxybutyl (meth)acrylate, etc.; acetoacetoxymethyl (meth)acrylate; acrylamides, such as acrylamide, methacrylamide, N-methyl acrylamide, N, N-dimethyl acrylamide, N-methyl methacrylamide, N, N-dimethyl methacrylamide, N-methylol acrylamide, N-methylol methacrylamide and diacetone acrylamide, etc.; mono- or dialkylaminoalkyl (meth)acrylate, such as mono- or dimethylaminoethyl (meth)acrylate, mono- or diethylaminoethyl (meth)acrylate, mono- or dimethylaminopropyl (meth)acrylate, mono- or diethylaminopropyl (meth)acrylate, etc.; and ethylenically unsaturated carboxylic acids, such as acrylic acid, methacrylic acid, crotonic acid, maleic acid, itaconic acid and citraconic acid, etc. These functional group-containing monomers may be used singly or in combination of two or more.

The functional group-containing monomer is usually preferably 0.1 to 5.0 mass %, more preferably 0.3 to 5.0 mass %, and most preferably 0.5 to 3.0 mass %, with respect to the total amount of the monomer. Within these ranges, the conductive adhesive agent composition is stable and the adhesion between the conductive layer formed of the conductive adhesive agent composition and the stretchable base material 31 are good. Examples of the other monomers include vinyl esters, such as vinyl acetate and vinyl propionate, etc.; olefins such as ethylene, propylene and isobutylene, etc.; halogenated olefins, such as vinyl chloride and vinylidene chloride, etc.; styrenic monomers, such as styrene and α-methylstyrene; diene monomers, such as butadiene, isoprene and chloroprene; and nitrile-based monomers such as acrylonitrile and methacrylonitrile, etc. These may be used singly or in combination of two or more. The other monomers are usually contained in a content of preferably 0.1 to 5.0 mass %, more preferably 0.3 to 5.0 mass %, and most preferably 1.0 to 3.0 mass %, with respect to the total amount of the monomers.

As the emulsifier, those normally used for emulsion polymerization can be used, and there is no particular limitation. Examples of the emulsifier that can be used include known emulsifiers, including anionic type reactive emulsifiers each having a radically polymerizable functional group, such as a vinyl group, a propenyl group, an isopropenyl group, a vinyl ether group and an allyl ether group; nonionic type reactive emulsifiers; or non-reactive emulsifiers, etc. Examples of the non-reactive emulsifier include anionic emulsifiers, such as sodium lauryl sulfate, ammonium lauryl sulfate, sodium dodecylbenzene sulfonate, sodium polyoxyethylene lauryl sulfate, sodium polyoxyethylene alkyl ether sulfate, ammonium polyoxyethylene alkylphenyl ether sulfate, sodium polyoxyethylene alkylphenyl ether sulfate and sodium polyoxyethylene alkyl sulfosuccinate, etc., and nonionic emulsifiers, such as polyoxyethylene alkyl ether, polyoxyethylene alkylphenyl ether, polyoxyethylene fatty acid esters and polyoxyethylene polyoxypropylene block polymers, etc.

Examples of the anionic reactive emulsifier include commercially available products, such as "Adecalia Soap SE-20N", but are not particularly limited thereto as long as they have reactivity. Examples of the nonionic reactive emulsifier include commercially available products, such as "Adecalia Soap NE-10", but are not particularly limited thereto as long as they have reactivity. A used amount of these emulsifiers is preferably 0.1 to 8.0 parts by mass, and more preferably 0.5 to 5.0 parts by mass, with respect to 100 parts by mass of a mixture of the above-mentioned monomers as an active ingredient (excluding solvents and various additives). If the used amount is within this range, emulsion polymerization is stable, and storage stability and machine stability of the obtained aqueous emulsion adhesive agent are good. The conditions of emulsion polymerization are not particularly limited, and the conditions applied in the normal emulsion polymerization can be adopted as they are. Generally, after an atmosphere in the reactor is replaced with an inert gas, the temperature is increased while stirring under reflux, and polymerization is performed in a temperature range of about 40 to 100° C. for about 1 to 8 hours after the increase in temperature is started.

When the aqueous emulsion adhesive agent is prepared by emulsion polymerization, a polymerization initiator is usually used. As the polymerization initiator, an azo-based type, such as 2,2'-azobis (2-methylpropionamidine) dihydrochloride; a persulfate, such as potassium persulfate; and a peroxide such as benzoyl peroxide can be used. A preferred concentration of the acrylic copolymer in the acrylic emulsion adhesive agent is usually 30 to 70% by mass. Further, the weight average molecular weight of the acrylic copolymer is preferably 100,000 to 3,000,000 in terms of adhesiveness and the like, and more preferably 400,000 to 2,000,000. Preferably, the alkalinity of the aqueous emulsion adhesive is not strongly basic. If the alkalinity of the aqueous emulsion adhesive agent is strongly basic, the electro-conductive organic polymer compound may precipitate when the electro-conductive organic polymer compound is formulated. The alkalinity of the aqueous emulsion adhesive agent is preferably less than pH 13.

The average particle diameter of emulsion particles of the aqueous emulsion adhesive agent is about 100 to 500 nm, and preferably 100 to 300 nm. If the average particle diameter is within such a range, it is possible to obtain an adhesive agent which is excellent in balance among emulsion polymerization stability and storage stability and machine stability of the resulting emulsion. The average particle diameter in this range enables one to obtain stable emulsion particles and prevent a used amount of the emulsifier from increasing. The average particle diameter of emulsion particles can be controlled by the type and concentration of an emulsifier to be added at the time of polymerization, or the concentration of a polymerization initiator, and the like. In the present embodiment, various known additives, such as antifoaming agents, preservatives, rust inhibitors, solvents, tackifiers, stabilizers, thickeners, crosslinking agents, plasticizers, wetting agents, fillers such as inorganic powders and metallic powders, pigments, coloring agents, ultraviolet ray-absorbers, etc. can be added to the aqueous emulsion adhesive agent, as required.

Subsequently, manufacturing of the adhesive sheet 10 by using the adhesive agent layer 3 produced by the above-described adhesive materials is described. Here, the adhesive agent layer 3 was formed using an acrylic adhesive of one-liquid aqueous emulsion type as the adhesive material. The acrylic adhesive agent of one-liquid aqueous emulsion type used in the present embodiment contains 50 to 60% of water and 40 to 50% of an acrylic ester-based copolymer compound. In the present embodiment, PEDOT: PSS was formulated as the electro-conductive organic polymer compound into the adhesive materials as described above.

In the present embodiment, first, the acrylic adhesive agent and PEDOT: PSS are mixed. At this time, in the present embodiment, a commercially available solution of PEDOT: PSS may be concentrated beforehand so that the viscosity thereof is matched with the viscosity suitable for coating of the adhesive material. Alternatively, a solution of PEDOT: PSS having a suitable viscosity may be purchased. In the present embodiment, it is preferable that the content of PEDOT: PSS in a PEDOT solution is about 3% by mass when mixed with the acrylic adhesive agent. Mixing an acrylic adhesive agent with PEDOT and PSS may be performed manually or by using a device such as a magnetic stirrer. Hereinafter, the adhesive material in the context of the present embodiment refers to a material obtained by mixing at least an acrylic adhesive agent, PEDOT and PSS.

Subsequently, in the present embodiment, the above-mentioned adhesive material is applied to the second releasing sheet 2. At this time, the second releasing sheet 2 may be a releasing sheet provided with processing, such as a coating or formation of a barrier layer, as described above. The coating may be performed by a method using an adhesive material as ink, such as a screen printing method or an ink jet printing method. Further, the coating may be performed by a bar coating method, a slit coating method, a die coating method, a blade coating method, a roll coating method, a dip coating method and a spin coating method, etc. Further, in the present embodiment, the adhesive material is not limited to being applied to the second releasing sheet 2, but may be applied to the first releasing sheet 1. The first releasing sheet 1 and the second releasing sheet 2 may contain the same material or may contain different materials. In addition, the first releasing sheet 1 and the second releasing sheet 2 may be sheets which have been subjected to the same treatment or sheets which have been subjected to different treatments.

The thickness of the adhesive agent layer 3 is not particularly limited. For example, the thickness of the adhesive agent layer 3 is preferably 30 μm or less, more preferably 25 μm or less, and most preferably 20 μm or less. Such thicknesses can lower the resistivity in the thickness direction of the adhesive agent layer 3, and this enables biosignals in a higher-quality to be easily obtained. Further, it is preferable that the film thickness of the adhesive agent layer 3 is thinner as a residue of the adhesive agent layer 3 is less likely to remain on the skin surface when the adhesive agent layer 3 is peeled off from the skin surface.

Additionally, a thinner film thickness is preferable, because pain at the time of peeling can be reduced. Further, the thinner the film thickness of the adhesive agent layer 3, the less adhesive material is required to form the adhesive agent layer 3, and this enables the cost of the adhesive sheet 10 to be lowered, and accordingly the cost of a biosensor 101 to be lowered. The lower limit of the film thickness of the adhesive agent layer 3 is not particularly limited, but is preferably 5 μm or more, and more preferably 10 μm or more, for example, because an adhesive agent layer 3 having a uniform film thickness can be stably formed.

Subsequently, in the present embodiment, the first releasing sheet 1 to which an adhesive material is applied is dried in a drying step. In the drying step of the present embodiment, the first releasing sheet 1 is placed in a hot air oven and dried under conditions of 105° C. and 75 seconds or more. The adhesive material is dried so that the amount of PEDOT contained in the adhesive material is, e.g., 2.2 wt %. The drying step converts the adhesive material into the adhesive agent layer 3. The first releasing sheet 1 is applied to the adhesive agent layer 3.

Subsequently, in the present embodiment, the adhesive agent layer 3 to which the first releasing sheet 1 and the second releasing sheet 2 have been applied is cured at room temperature for 24 hours. In the acrylic adhesive agent, a main agent is linked with a crosslinking agent by curing and physical and chemical properties of the acrylic adhesive change. Crosslinking reactions differ depending on the temperature and reaction time during curing. After curing, the adhesive agent layer 3 of the adhesive sheet 10 of the present embodiment acquires required adhesiveness and is completed.

The completed adhesive sheet 10, the first releasing sheet of which is peeled off from the adhesive agent layer 3, is applied to the undersurface of the wiring board 100. The wiring board 100 including the adhesive agent layer 3 to which the second releasing sheet 2 is affixed is provided to end users as a biosensor 101. The second releasing sheet 2 of the biosensor 101 is peeled off when used by an end user, and the biosensor 101 is applied to the skin surface S of the subject through adhesive agent layer 3. Since the adhesive agent layer 3 is electrically conductive because it contains an electro-conductive organic polymer compound, as described above, biosignals obtained from the skin surface S can be transmitted to an electrode 33. Additionally, such an adhesive agent layer 3 has anisotropy in conductivity, and the anisotropy is exhibited in high resistance in the in-plane direction and low resistance in the thickness direction of the adhesive agent layer 3. For this reason, in the wiring board 100 to which the adhesive agent layer 3 is applied, biosignals obtained from the skin surface S are properly guided toward the stretchable wiring 32 through the adhesive agent layer 3, and are inputted to an element (not shown).

In the adhesive sheet 10 of the present embodiment, as described above, the first releasing sheet 1 is first peeled off from the adhesive agent layer 3, and the second releasing sheet 2 is later peeled off from the adhesive agent layer 3. To this end, in the present embodiment, while supporting the second releasing sheet 2, the adhesive agent layer 3 is positioned inwardly, and a force is applied to the first releasing sheet 1 in the outward direction. At this time, in order to prevent a situation in which the adhesive agent layer 3 remains on the first releasing sheet 1 side and the second releasing sheet 2 peels off from the adhesive agent layer 3, the adhesive sheet 10 is configured such that the adhesive force between the front surface 3a of the adhesive agent layer 3 and the first releasing sheet 1 is weaker than the adhesive force between the back surface 3b and the second releasing sheet 2.

The adhesive agent layer 3 is a single layer between the first releasing sheet 1 and the second releasing sheet 2. In this context, the "single layer" means that there is no border in a portion present between the first releasing sheet 1 and the second releasing sheet 2 of the adhesive agent layer 3. The border refers to a boundary line between the same members or different members. Namely, the adhesive agent layer 3 is a layer made of the same member (not including any other material) in the thickness direction. Such an adhesive agent layer 3 does not include a layer obtained by impregnating a nonwoven fabric, etc. with an adhesive material, or a layer obtained by coating both sides of nonwoven fabric, etc. with an adhesive material. By configuring the adhesive agent layer 3 in this manner, thinning can be easily achieved in the present embodiment, and this enables living body contact impedance or pain of the subject when the wiring board 100 is removed to be reduced. Changing adhesive force between the front surface 3a and the back surface 3b of the adhesive agent layer 3, which is a single layer, is achieved by changing the states of the faces facing the adhesive agent layer 3 of the first releasing sheet 1 and the second releasing sheet 2, respectively. The states of the first releasing sheet 1 and second releasing sheet 2 can be modified by selecting materials of the first releasing sheet 1 and the second releasing sheet 2 or by surface processing. Examples of processing include, for example, coating of the above-mentioned releasing agent.

In the present embodiment, the adhesive force of the back surface 3b of the adhesive agent layer 3 to be applied to the skin surface of the subject is set to a range of, for example, 0.05 N/mm or more and 1.0 N/mm or less, and more preferably 0.08 N/mm or more and 0.3 N/mm or less. By setting the adhesive force of the back surface 3b against the skin surface within such a range, the adhesive sheet 10 of the present embodiment can patch the wiring board 100 to the skin surface of the subject and to prevent the wiring board 100 from shifting or dropping, and further, to reduce pain to the subject when the wiring board 100 is removed. The above adhesive force was evaluated in accordance with a test method of JIS Standard Z0237 (adhesive force). In this test, the stretchable base material 31 of the wiring board 100, which is to be applied to the skin surface of the subject, is applied to the front surface 3a of the adhesive agent layer 3, and the obtained laminated product was used as a sample.

As described above, in the present embodiment, the adhesive agent layer 3 is not formed on the wiring board 100, but is constituted as an independent adhesive sheet 10. Therefore, in the present embodiment, even if there is a step such as curing that requires a relatively long time in the process of manufacturing the adhesive agent layer 3, it is possible to supply the adhesive sheet 10 that has undergone such a step to a manufacturing side of the biosensor 101. Since a manufacturer of the biosensor 101 peels off the first releasing sheet 1 of the adhesive sheet 10, and then applies it to the wiring board 100 to complete the biosensor 101, it is possible to increase throughput of the biosensor 101 production. In addition, the adhesive sheet 10 of the present embodiment can be used not only for a biosensor 101 for detecting an electric signal outputted from a living body but also for EMS (Electrical Muscle Stimulation) devices for providing an electric signal to a living body. Since the adhesive sheet 10 exhibits a higher adhesiveness to the living body than known adhesive sheets of hydrogels and the like, it is possible to prevent the EMS device from peeling off from the living body even if the user moves during use of the EMS device. In addition, since the adhesive sheet 10 has an electro-conductivity equivalent to that of known adhesive sheets, electrical signals can be efficiently transmitted to the living body to give a good stimulus to the muscle because of the higher adhesiveness to the living body. Further, the adhesive sheet 10 of the present embodiment can be applied to the EMS device each time the EMS device is used, and can be peeled off and made disposable after the EMS device is used. Therefore, it can be said that the EMS device using the adhesive sheet 10 is preferable in terms of hygiene aspect to known EMS devices on the assumption that the pads are used a plurality of times.

EXAMPLES

Figure 4:
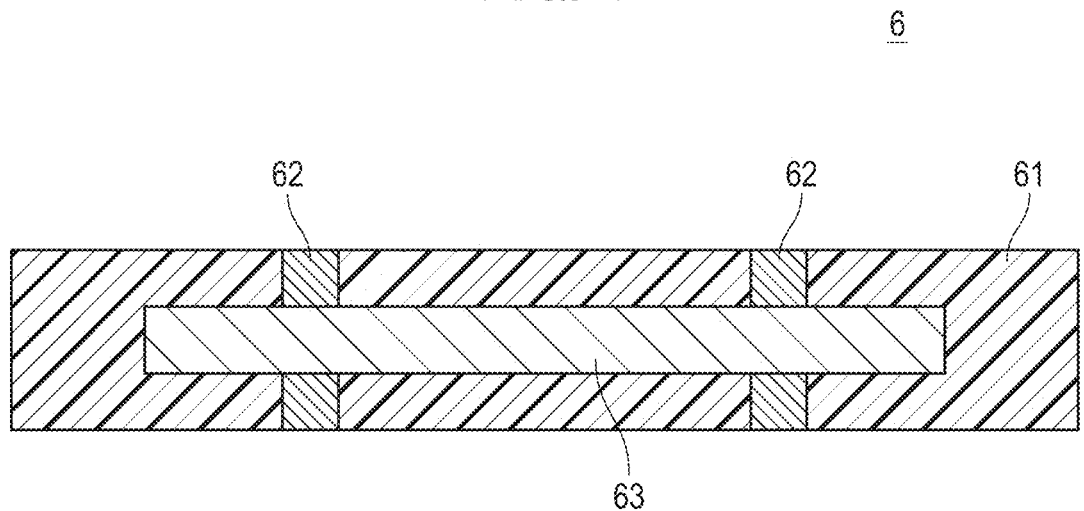
FIG. 4 is a schematic diagram for explaining an element used for detecting an electric characteristic in an Example of the present invention.

Subsequently, the Examples of the adhesive sheet 10 of the present embodiment described above are described. In the present Examples, the above-mentioned adhesive agent layer 3 is applied to a wiring board 100 to produce a biosensor for experimentation, and electric characteristics of signals obtained by the biosensor are detected by an element. FIG. 4 is a schematic diagram for explaining an element 6 used for detecting electric characteristics in the present Examples. The element 6 comprises a film base material 61 typified by PET or the like; two silver (Ag) electrodes 62 formed by printing on the film base material 61 in a spaced-apart manner; and a wiring 63 made of an adhesive agent layer 3 and attached so as to connect the respective silver (Ag) electrodes 62.

The inventors of the present invention produced five types of adhesive agent layers 3 by changing the processing conditions, forming each of the adhesive agent layers 3 into a wiring 63, and measured electric characteristics (resistivity) thereof. The production conditions of the five types of adhesive agent layers 3 are shown in Table 1. In Table 1, the five types of adhesive agent layers 3 are denoted as Nos. 1 to 5. The preparation conditions of the adhesive agent layers 3 of No. 1 to No. 5 are as shown in Table 1 below. Namely, each of the adhesive agent layers 3 of No. 1 to No. 5, was a mixture of a member having conductivity obtained by mixing PEDOT: PSS, $H_2O$, and IPA (IsoPropyl Alcohol) with Oribain® BPW HW-1 (product name). In the present Examples, PEDOT: PSS in the state of powder (manufactured by Sigma Aldrich, product name: 768618-5G) and PEDOT: PSS in the state of liquid (manufactured by Sigma Aldrich, product name: 739324-100G) were used as PEDOT: PSS. As the PEDOT: PSS in the state of powder, commercially available PEDOT: PSS was concentrated to approximately 3 wt %, and this was mixed by manual agitation with $H_2O$ and IPA. The wiring 63 was dried at 105° C. for 75 seconds or more, and the curing condition was at room temperature for 24 hours.

TABLE 1

| No | PEDPT:PSS | Content (After drying) % | Others |
|----|-----------|--------------------------|--------|
| 1  | Powder    | 1.2                      |        |
| 2  |           | 2.2                      |        |
| 3  |           | 8.6                      | Silver-coated powder added (10%) |
| 4  |           | 2.2                      |        |
| 5  | Liquid    | 2.2                      |        |

In the adhesive agent layers 3 of No. 1 to No. 4, a powder of PEDOT: PSS was used. Of No. 1 to No. 4, the adhesive agent layer 3 of No. 2 and the adhesive agent layer 3 of No. 4 contained 2.2% (weight ratio) of PEDOT: PSS after drying, the adhesive agent layer 3 of No. 1 contained 1.2% (weight ratio) of PEDOT: PSS after drying, and the adhesive agent layer 3 of No. 3 contained 8.6% (weight ratio) of PEDOT: PSS after drying. Of these, silver-coated powder (manufactured by Sigma Aldrich, product name: 327077-10G) was added only to the adhesive agent layer 3 of No. 4 at a weight ratio of 10% (weight ratio). The silver-coated powder is produced by direct plating without an underlayer, and has high conductivity inherent to silver. The adhesive agent layer 3 of No. 5 was produced using liquid PEDOT: PSS. The liquid PEDOT: PSS is, for example, a 1.1% neutral aqueous solution of poly(3,4-ethylenedioxythiophene)-poly (styrenesulfonate).

The inventors of the present invention measured average contact impedance, adhesive force and noises of the adhesive agent layer 3 as characteristics of the adhesive agent layer 3 required for application to biosensor 101. Table 2 shows the average contact impedance and the adhesive force. Table 3 shows hum noise and noise floor. It should be noted that the impedances were measured by inputting rectangular waves of 10 Hz (+0.04 μA).

TABLE 2

|   | Film thickness (μm) | Average contact impedance (kΩ) | Adhesive force (N/mm) |
|---|---------------------|--------------------------------|-----------------------|
| 2 | 10                  | 97                             | 0.08 (Good)           |
|   | 11                  | 154                            | 0.09 (Good)           |
|   | 12                  | 66                             | 0.13 (Good)           |
|   | 13                  | 101                            | 0.16 (Good)           |
|   | 14                  | 120                            | 0.23 (Good)           |
|   | 16                  | 155                            | 0.28 (Good)           |
| 3 | 10                  | 19                             | 0.02 (Weak)           |
| 4 | 28                  | 21                             | 0.43 (Strong)         |
| 5 | 10                  | 64                             | 0.23 (Good)           |

TABLE 3

| Group | No | Film thickness (μm) | Hum noise (dBuV) @60 Hz/50 Hz | Noise floor (dBuV) @54.5-55.5 Hz |
|-------|----|---------------------|-------------------------------|----------------------------------|
| A     | 2  | 10                  | 14                            | −18                              |
|       |    | 13                  | 14                            | −14                              |
|       |    | 14                  | 11                            | −15                              |

TABLE 3-continued

| Group | No | Film thickness (μm) | Hum noise (dBuV) @60 Hz/50 Hz | Noise floor (dBuV) @54.5-55.5 Hz |
|---|---|---|---|---|
| | Reference Example | — | 17 | −23 |
| B | 2 | 10 | 11 | 1.8 |
| | | 11 | 10 | 4.4 |
| | | 16 | 15 | −3 |
| | Reference Example | — | 15 | −25 |
| C | 5 | 14 | 10 | −18 |
| | | 14 | 10 | −16 |
| | Reference Example | — | 6 | −9 |

The "Reference Examples" shown in Table 3 show the electric characteristics obtained by applying a biosensor to the skin of a subject using TEN 20 (trademark). Such a water-containing gel paste is an agent conventionally applied to the back surface of a biosensor and used to detect biosignals. TEN 20 (trademark) is used by being manually applied to the electrode of a biosensor. The hum noises and noise floor shown in Table 3 vary relatively greatly depending on time that has elapsed since the adhesive agent layer 3 was produced or on environments. Therefore, the present inventors produced biosensors 101 by using the adhesive agent layer 3 in the adhesive sheet 10 and biosensors coated with TEN 20 in the same environment on the same day, and those produced in the same environment on the same day were classified into groups A, B, and C. The electrical characteristics of the adhesive agent layer 3 were evaluated using as a reference the electrical characteristics of the biosensors which belonged to the same group and which were produced by using the TEN 20.

The average contact impedance, the hum noises and the floor noises were measured by producing the biosensor 101 shown in FIG. 1 and using the adhesive agent layer 3 in the adhesive sheet 10 of this biosensor 101. An index for impedance between the adhesive agent layer 3 and the skin surface S can be obtained from the contact impedance. An index for noise of the signals from a biosensor using an adhesive agent layer can be obtained from the hum noise and noise floor. The contact impedance shown in Table 2 is a value obtained when AC signals of 10 Hz were applied to the electrodes 62, and is an average value of measurements performed a plurality of times. The hum noise is a value indicating the strength of noise when there is an external AC power source at 50 Hz or 60 Hz (mainly from power frequency sources in Japan). The noise floor indicates the strength of noise that does not overlap with hum noise in the range of 54.5 Hz to 55.5 Hz or targeted biosignal frequencies. An index for the sensitivity of the biosensor 101 using the adhesive agent layer 3 can be obtained by the contact impedance. In addition, an index for noise in signals obtained from the biosensor 101 using the adhesive agent layer 3 can be obtained by the hum noise and the noise floor. Quantitative measurements of adhesive force were performed according to JIS Z 0237 standards. Sensory assessments of adhesive force were performed by applying fingers to the adhesive agent layer 3 about three to five times, or by actually applying the adhesive agent layer 3 to the living body to examine tactile feel at the time of peeling.

As shown in Table 2, the present inventors varied the film thickness of the adhesive agent layer 3 of No. 2 from 10 μm to 16 μm. In the adhesive agent layer 3 of No. 2, a good adhesive force could be obtained regardless of the film thickness. Further, with the adhesive agent layer 3 of No. 5, a good adhesive force could be also obtained. On the other hand, the adhesive agent layer 3 of No. 3 was difficult to be applied to the biosensor 101 because of its weak adhesive force. This is considered to be due to the fact that the adhesive agent layer 3 of No. 3 contained PEDOT: PSS in a larger amount than the adhesive agent layer 3 of No. 2. Conversely, the adhesive agent layer 3 of No. 4 resulted in pain when peeled off from the living body because of its strong adhesive force. This is considered to be due to the thickness of the adhesive agent layer 3 of No. 4 being as thick as 28 μm. Incidentally, the adhesive agent layer 3 of No. 4 contained silver-coated powder, and this point is considered to act to lower the adhesiveness. From this, it can be inferred that contribution of thickness of a film to adhesiveness is significant.

From the results shown in Table 2, the thickness of the adhesive agent layer 3 of the embodiment described above is preferably equal to or less than 25 μm, and more preferably equal to or less than 20 μm. From the results shown in Table 2, it can be seen that the adhesive force of the adhesive agent layer 3 against a living body ranges from 0.05 N/mm or more and 1.0 N/mm or less, and more preferably from 0.08 N/mm or more and 0.3 N/mm or less, as described above. Such adhesive force can be adjusted by the thickness of the adhesive agent layer 3, and by changing the amount of PEDOT: PSS or adding silver-coated powder within an allowable range of electric characteristics.

As shown in Table 2, the adhesive agent layer 3 of each of the present Examples has a contact impedance of 200 kΩ or less in all biosensors 101. Although such a value of the adhesive agent layer 3 can be said to be high in light of the contact impedance obtained from the conducting paste TEN 20 (trademark, manufactured by Weaver and Company) used in known biosensors being about 22 kΩ, it is sufficiently applicable to the biosensor 101. Namely, the contact impedance between the adhesive agent layer 3 and the skin is preferably equal to or less than 200 kΩ, more preferably equal to or less than 150 kΩ, and most preferably equal to or less than 70 kΩ, as measured by inputting rectangular waves of 10 Hz (±0.04 μA). Upon focusing on the contact impedance, the adhesive agent layers 3 of No. 3 and No. 4 are particularly preferred, but the adhesive agent layers 3 of No. 3 and No. 4 are unsuitable in terms of adhesive force as described above. Based on the above, it has been found that according to the present Examples, the adhesive agent layers 3 of No. 2 and No. 5 are applicable to the biosensor 101.

Figure 5A:
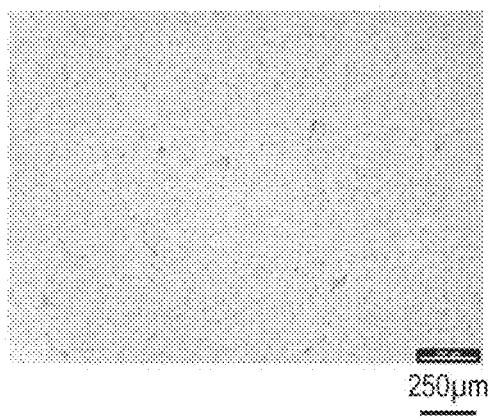
FIGS. 5(a) to 5(d) are drawings showing the results of microscopic observations of the adhesive materials from above prior to drying the adhesive agent layer.
Figure 5B:
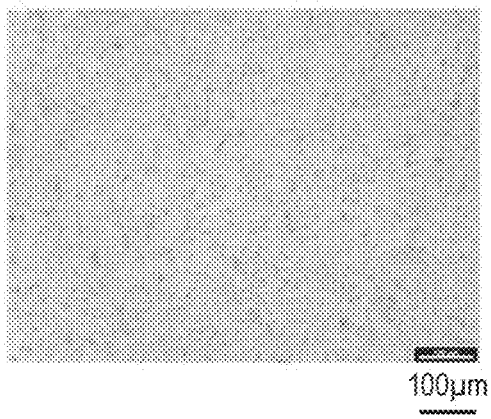
Figure 5C:
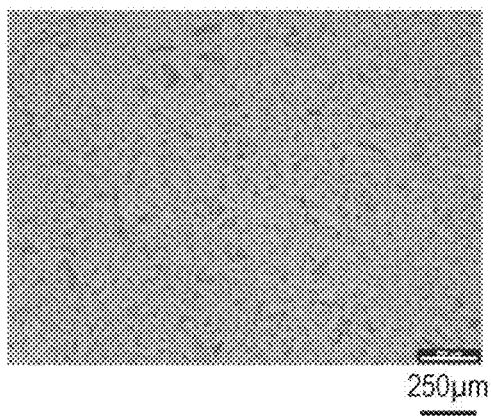
Figure 5D:
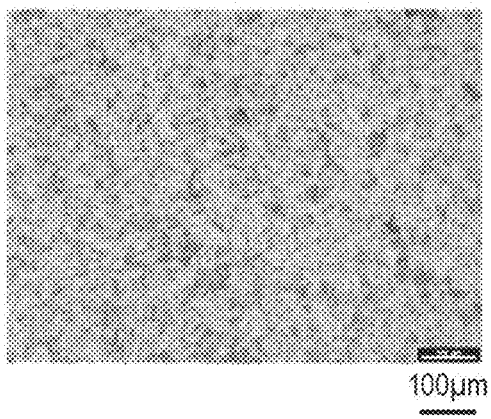
Figure 6A:
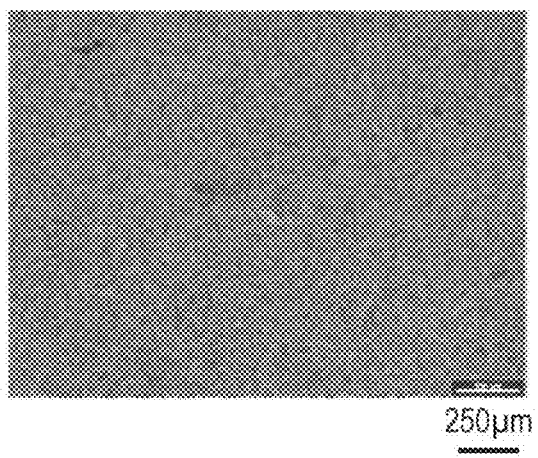
FIGS. 6(a) to 6(c) are diagrams showing the results of microscopic observations of the adhesive materials from above prior to drying the adhesive agent layer.
Figure 6B:
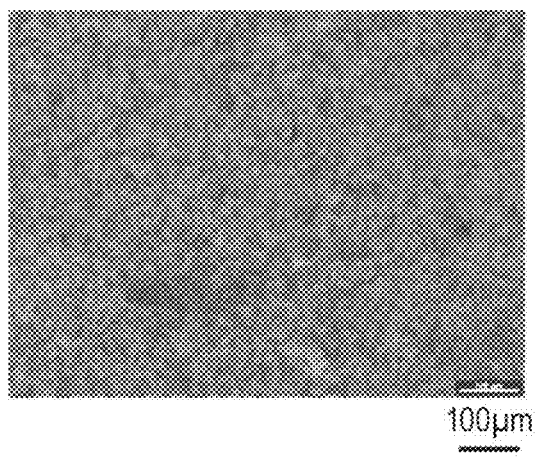
Figure 6C:
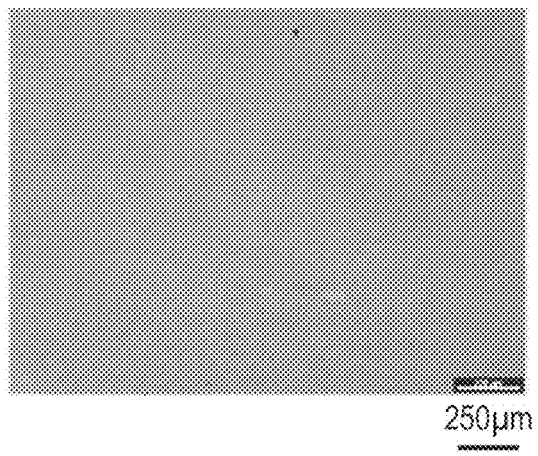

In addition, as shown in Table 3, the hum noise and noise floor of the adhesive agent layers 3 of No. 2 and No. 5 are both in appropriate ranges to be used in the biosensor 101. The present inventors focused on the fact that despite the fact that the film thickness (14 μm) and the PEDOT: PSS content were equal between the adhesive agent layers 3 of No. 2 and No. 5, only the adhesive agent layer 3 of No. 5 exhibited a lower noise floor than the Reference Examples. Further, since the production conditions of the adhesive agent layer 3 of No. 2 and the adhesive agent layer 3 of No. 5 differ from each other in whether the PEDOT: PSS is in the state of powder or in the state of liquid, the present inventors observed the state of diffusion of the PEDOT: PSS into liquid. FIG. 5(a) to FIG. 6(c) are diagrams showing the results of the observation of adhesive material of the adhesive agent layer 3 from above by a microscope prior to drying. FIG. 5(a) and FIG. 5(b) show the adhesive material of No. 1, and FIG. 5(b) shows FIG. 5(a) in a further enlarged manner. FIG. 5(c) and FIG. 5(d) show the adhesive material of No. 2, and FIG. 5(d) shows FIG. 5(c) in a further enlarged manner. FIG. 6(a) and FIG. 6(b) show the adhesive material of No. 3, and FIG. 6(b) shows FIG. 6(a) in a further enlarged manner. FIG. 6(c) shows the adhesive material of No. 5.

According to FIG. 5(a) to FIG. 6(c), members derived from PEDOT: PSS aggregate in "island-like state" in the adhesive material, and the aggregation is more noticeable in the adhesive material of No. 2 shown in FIG. 5(c) and FIG. 5(d). In order to quantitatively measure the degree of aggregation, the present inventors observed island-like portions, and measured the diameters (particle diameters) by approximating the portions as substantially circular "particles" and averaged the obtained diameters. Furthermore, the present inventors calculated the ratio of an area occupied by the island-like portions in the viewing area (field of view of microscope) of the adhesive material. The results are shown in Table 4 together with the volume resistivities of the respective adhesive agent layers 3. The volume resistivity was measured a plurality of times using the element 6 shown in FIG. 4, and the average thereof was calculated. The volume resistivity was measured after curing for 24 hours. The measured volume resistivities are shown in Table 4 as a result of DC conversion.

TABLE 4

| No | Average volume resistivity (Ωcm) | Average particle diameter (μm) | Average area % |
|---|---|---|---|
| 1 | — | 17 | 19 |
| 2 | 12800 | 83 | 44 |
| 3 | 700 | — | 83 |
| 5 | 15260 | — | 90 |

According to Table 4, the volume resistivity of the adhesive agent layer of No. 2 was 12, 800 Ωcm, the volume resistivity of the adhesive agent layer of No. 3 was 700 Ωcm, and the volume resistivity of the adhesive agent layer of No. 5 was 15, 260 Ωcm. The volume resistivity includes both a resistance value in the in-plane direction and a resistance value in the thickness direction of the adhesive agent layer. Further, according to Table 1, the contents of PEDOT: PSS in the dried adhesive agent layers of No. 2 and No. 5 were both 2.2%. Therefore, the adhesive agent layers of No. 2 and No. 5, which contain substantially the same extent of PEDOT: PSS, which is a conductive member, are considered to have substantially the same values of the volume resistivity. Further, according to Table 4, it can be seen that the adhesive material of No. 3 containing 8.6% of PEDOT: PSS is so densely packed that the particle size of PEDOT: PSS is indistinguishable, and the adhesive material of No. 5 containing 2.2% of PEDOT: PSS is so dispersed that the particle size of PEDOT: PSS is indistinguishable.

According to Table 4, it was found that the particle size of the aggregate was relatively large in the adhesive agent layer of No. 2, and 44% of the observed area was occupied by a member derived from PEDOT: PSS. From these results and the result that the contact impedance of the adhesive agent layer of No. 2 shown in Table 2 is higher than that of the other elements, it is considered that the conductive member in the adhesive material of the adhesive agent layer of No. 2 is an island-like shape, resulting in a smaller contact area, and this increases the contact impedance. Further, the present inventors believe that the diameter of the island-like portions in adhesive material of No. 2 is larger than that of the adhesive material of the other elements, and the PEDOT: PSS is not sufficiently dispersed in Oribain® BPW HW-1. Furthermore, the present inventors believe that the degree of dispersion of the adhesive material affects noise-relating characteristics of the adhesive agent layer.

Further, according to Table 2, although the adhesive agent layer of No. 5 contains PEDOT: PSS of the same level as the adhesive agent layer of No. 2, the contact impedance with the skin is lower than the adhesive agent layer of No. 2. The contact impedance with the skin shows thickness-direction resistivity of the adhesive agent layer, and is a factor having a large effect on the contact area between the skin and the conductive adhesive agent layer. As shown in FIG. 6(c) and Table 4, in the adhesive agent layer of No. 5, members derived from PEDOT: PSS do not aggregate and are dispersed in the adhesive agent, and the ratio of the area of the member including PEDOT: PSS is sufficiently larger than that of the adhesive agent layer of No. 2. Therefore, in the present Examples, it is considered that the conductivity in the thickness direction is increased and the electric conductivity in the in-plane direction is lowered in the adhesive agent layer of No. 5. In this respect, the present inventors believe that the anisotropic conductivity of the adhesive agent layer can be controlled by controlling the degree of aggregation and dispersion of the adhesive material.

Variation Example

Subsequently, the Variation Example of the above-described embodiment is described below. In the Variation Example, the adhesive agent layers are provided only in the portions of electrodes 33 of the wiring board 100, whereas the adhesive agent layer 3 is applied to the entire back surface of the wiring board 100 in the configuration shown in FIGS. 1(a) and 1(b).

Figure 7:
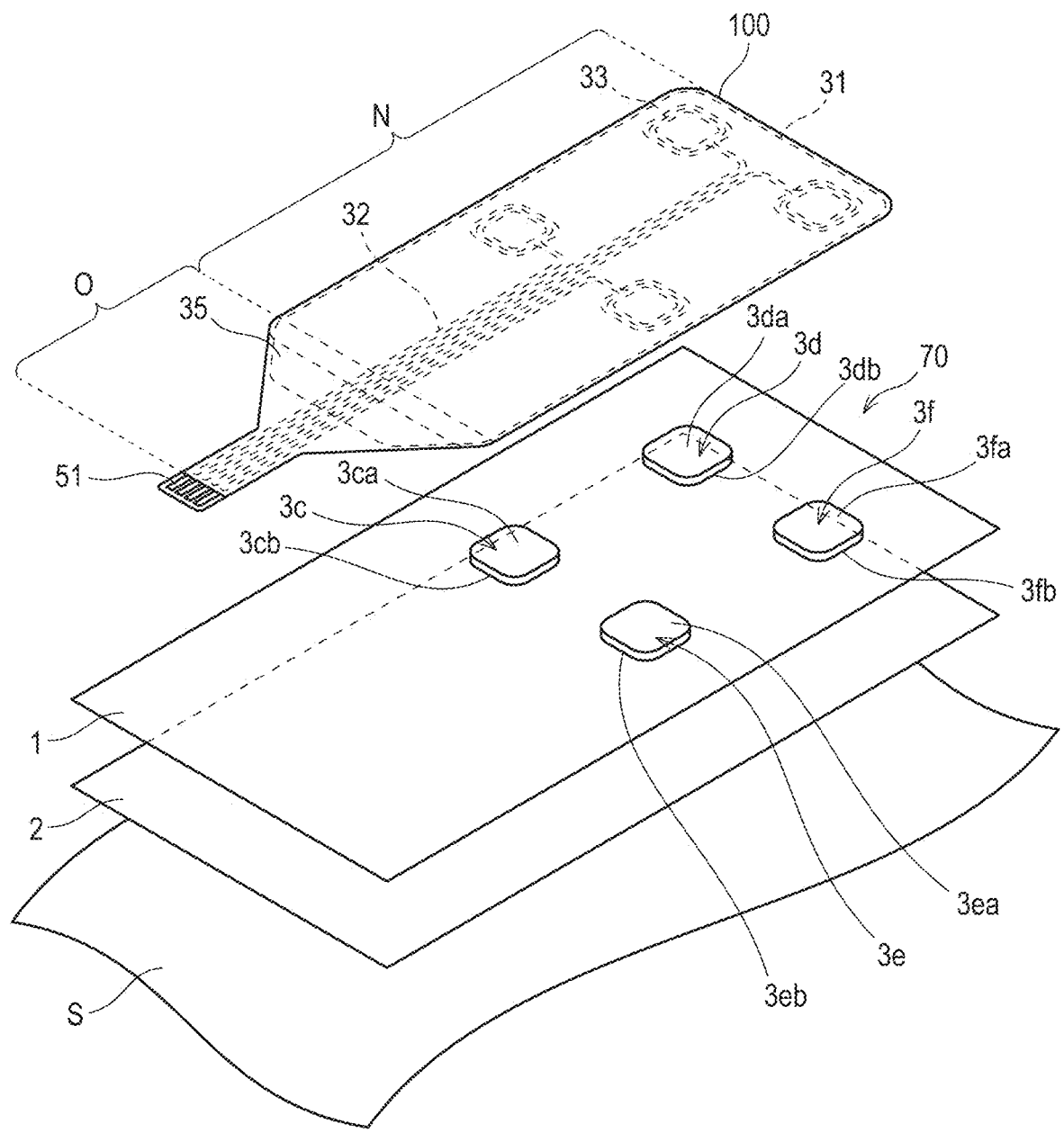
FIG. 7 is a diagram for explaining an adhesive sheet of a Variation Example of the embodiment shown in FIG. 1.

FIG. 7 is a diagram for explaining the adhesive sheet 70 of the Variation Example. The adhesive sheet 70 has adhesive agent layers 3c, 3d, 3e and 3f. The adhesive agent layers 3c, 3d, 3e and 3f constitute a plurality of islands isolated from each other. In this context, "isolated from each other" means that there are no portions that contact or intersect each other in all of a plurality of adhesive agent layers 3c, 3d, 3e and 3f. In the adhesive agent layers 3c, 3d, 3e and 3f, the respective front surfaces 3ca, 3da, 3ea and 3fa are applied to the back surface of the wiring board 100, and the respective back surfaces 3cb 3db, 3eb and 3fb are applied to the skin surface S. The positions and shapes of the adhesive agent layers 3c, 3d, 3e and 3f each correspond to the positions and shapes of the four electrodes 33 of the wiring board 100, and the adhesive agent layers 3c, 3d, 3e and 3f each directly adhere to the electrodes 33.

The adhesive sheet 70 of the Variation Example is manufactured by, for example, the following method. Namely, in the Variation Example, similarly to the embodiment described above, an adhesive material is applied on the second releasing sheet 2 and dried to form the adhesive agent layer 3. Then, a third releasing sheet (not shown) different from the first releasing sheet 1 is applied to the top of the adhesive agent layer 3, and the adhesive agent layer 3 is press-punched together with the third releasing sheet. The press punching process is a process for removing an unnecessary part of the adhesive agent layer 3 other than the adhesive agent layers 3c, 3d, 3e and 3f. In the press punching process, a notch is made in the third releasing sheet and the adhesive agent layer 3 by a press machine (not shown). At this time, in the present Variation Example, the second releasing sheet 2 is also cut to a depth of about half or less than half of the thickness of the second releasing sheet 2, and the second releasing sheet 2 is half-cut. By such a step, in the present Variation Example, it is possible to securely remove unnecessary portions of the adhesive agent layer 3 from the second releasing sheet 2. Subsequently, in the present Variation Example, the portion excluding from the adhesive agent layer 3c to the adhesive agent layer 3f is removed from the press-punched adhesive agent layer 3. At this time, the third releasing sheet on the adhesive agent layer excluding from the adhesive agent layer 3c to the adhesive agent layer 3f is removed together with the adhesive agent layer. In addition, the third releasing sheet on from the adhesive agent layer 3c to the adhesive agent layer 3f is also removed and a first releasing sheet 1 is applied on from the adhesive agent layer 3c to the adhesive agent layer 3f.

Such a Variation Example can eliminate the possibility of short-circuiting between the electrodes 33 even when conduction anisotropy of the adhesive agent layer 3 is low, and can contribute to the provision of highly reliable biosensors.

The embodiment and the Examples include the following technical ideas. A first embodiment of the present invention is an adhesive sheet for use in applying a wiring board to a surface onto which the wiring board is to be applied, the adhesive sheet comprising an adhesive agent layer comprising an electro-conductive organic polymer compound and an adhesive material; a first releasing sheet provided on a first surface of the adhesive agent layer; and a second releasing sheet provided on a second surface corresponding to a back surface of the first surface in the adhesive agent layer.

A second embodiment of the present invention is the adhesive sheet as described in the first embodiment, in which the adhesive material is an electro-conductive adhesive agent composition comprising an aqueous emulsion adhesive agent. A third embodiment of the present application is the adhesive sheet as described in the first embodiment or the second embodiment, in which adhesive force between the first surface and the first releasing sheet is weaker than adhesive force between the second surface and the second releasing sheet.

A fourth embodiment of the present application is the adhesive sheet as described in any one of the first embodiment to the third embodiment, in which the adhesive agent layer is a single layer between the first releasing sheet and the second releasing sheet. A fifth embodiment of the present application is the adhesive sheet as described in any one of the first embodiment to the fourth embodiment, in which the adhesive agent layer has a plurality of islands isolated from each other.

A sixth embodiment of the present application is the adhesive sheet as described in any one of the first embodiment to the fifth embodiment, in which a thickness of the adhesive agent layer is 20 μm or less.

A seventh embodiment of the present application is the adhesive sheet as described in any one of the first embodiment to the sixth embodiment, in which adhesive force of the adhesive agent layer against a living body is 0.08 N/mm or more and 0.3 N/mm or less.

An eighth embodiment of the present application is the adhesive sheet as described in any one of the first embodiment to the seventh embodiment, in which contact impedance against a living body is 150 kΩ or less, when rectangular waves of 10 Hz and ±0.04 μA are supplied.

A ninth embodiment of the present application is the adhesive sheet as described in the second embodiment, in which the electro-conductive organic polymer compound is at least one type of polyanilines, polypyrroles, polythiophenes and derivatives thereof.

A tenth embodiment of the present application is the adhesive sheet as described in the ninth embodiment, in which the aqueous emulsion adhesive agent is an acrylic emulsion adhesive agent.

EXPLANATION OF REFERENCE NUMERALS

1 . . . First releasing sheet
2 . . . Second releasing sheet
3, 3c, 3d, 3e, 3f . . . Adhesive agent layer
3a, 3ca, 3da, 3ea, 3fa . . . Front surface
3b, 3cb, 3db, 3eb, 3fb . . . Back surface
6 . . . Element
10, 70 . . . Adhesive sheet
31 . . . Stretchable base material
32 . . . Stretchable wiring
33 . . . Electrode
35 . . . Film base material
51 . . . External terminal
61 . . . Wiring mask
62 . . . Electrode
63 . . . Wiring
100 . . . Wiring board
101 . . . Biosensor

What is claimed is:

1. An adhesive sheet attached to a wiring board, the adhesive sheet comprising:
    an adhesive agent layer comprising an electro-conductive organic polymer compound and an adhesive material; and
    a releasing sheet provided on a back surface of the adhesive agent layer,
    wherein the wiring board is attached on a front surface of the adhesive agent layer opposite the back surface of the adhesive agent layer, and configured for attachment to a surface of a living body to measure a biosignal of the living body,
    wherein the adhesive sheet has a contact impedance being less than 150 kΩ against the living body when rectangular waves of 10 Hz and ±0.04 μA are supplied,
    wherein the adhesive agent layer between the releasing sheet and the wiring board is a single layer,
    wherein a thickness of the adhesive agent layer is 12 μm to 14 μm,
    wherein the adhesive agent layer comprises poly(3,4-ethylenedioxythiophene) (PEDOT) as the electro-conductive organic polymer compound and polystyrene sulfonate ion (PSS),
    wherein an adhesive force of the front surface of the adhesive agent layer to the wiring board is different from an adhesive force of the back surface of the adhesive agent layer to the releasing sheet.

2. The adhesive sheet according to claim 1, wherein the adhesive material comprises an aqueous emulsion adhesive agent.

3. The adhesive sheet according to claim 2, wherein the aqueous emulsion adhesive agent is an acrylic emulsion adhesive agent.

4. The adhesive sheet according to claim 1, wherein the adhesive agent layer has a plurality of islands isolated from each other.

5. The adhesive sheet according to claim 1, wherein adhesive force of the adhesive agent layer against a living body is 0.08 N/mm or more and 0.3 N/mm or less.

6. The adhesive sheet according to claim 1, wherein the poly(3,4-ethylenedioxythiophene) (PEDOT) and the polystyrene sulfonate ion (PSS) in the adhesive agent layer are in liquid form.

7. The adhesive sheet according to claim 1, wherein the adhesive agent layer does not comprise silver-coated powder.

8. The adhesive sheet according to claim 1, wherein the adhesive agent layer does not comprise (a) a layer obtained by impregnating a nonwoven fabric and (b) a layer obtained by coating a nonwoven fabric.

9. A biosensor comprising the adhesive sheet attached to the wiring board according to claim 1.

10. A method of measuring a biosignal of a living body using the biosensor of claim 9.

11. The method of claim 10, wherein the adhesive material comprises an aqueous emulsion adhesive agent.

12. The method of claim 11, wherein the aqueous emulsion adhesive agent is an acrylic emulsion adhesive agent.

13. The method of claim 10, wherein the adhesive agent layer is a single layer.

14. The method of claim 10, wherein the adhesive agent layer has a plurality of islands isolated from each other.

15. The method of claim 10, wherein a thickness of the adhesive agent layer is 20 μm or less.

16. The method of claim 10, wherein adhesive force of the adhesive agent layer against a living body is 0.08 N/mm or more and 0.3 N/mm or less.

* * * * *